United States Patent

Kvarnström

[19]

[11] Patent Number: 5,906,488
[45] Date of Patent: May 25, 1999

[54] RELEASABLE HOLDING DEVICE PREVENTING UNDESIRABLE ROTATION DURING TIGHTENING OF A SCREW CONNECTION IN A BONE ANCHORED IMPLANT

[75] Inventor: Bjarne Kvarnström, Westmont, Ill.

[73] Assignee: Nobel Biocare AB, Goteborg, Sweden

[21] Appl. No.: 09/091,918

[22] PCT Filed: Dec. 23, 1996

[86] PCT No.: PCT/SE96/01751

§ 371 Date: Aug. 28, 1998

§ 102(e) Date: Aug. 28, 1998

[87] PCT Pub. No.: WO97/24997

PCT Pub. Date: Jul. 17, 1997

[30] Foreign Application Priority Data

Jan. 4, 1996 [SE] Sweden ................................ 9600041

[51] Int. Cl.⁶ ................................ A61L 1/16; A61L 3/06
[52] U.S. Cl. ........................ 433/116; 433/134; 433/127; 433/174; 433/229
[58] Field of Search ............................... 433/134, 50, 53, 433/75, 76, 116, 126, 127, 174, 141, 229, 114

[56] References Cited

U.S. PATENT DOCUMENTS

| | | | |
|---|---|---|---|
| 4,015,335 | 4/1977 | Nash et al. | 433/127 |
| 4,583,945 | 4/1986 | Labarde | 433/116 |
| 4,963,095 | 10/1990 | Weissman | 433/114 |
| 5,064,375 | 11/1991 | Jörnéus | 433/229 |

*Primary Examiner*—John J. Wilson
*Assistant Examiner*—Patrick Hilsmier
*Attorney, Agent, or Firm*—Pollock, Vande Sande & Amernick

[57] ABSTRACT

Holding device for use with a tool for mechanical tightening of a screw connection in a bone-anchored dental implant without the tissue which surrounds the implant being stressed, the holding device having a first part which rotationally locks to the implant, an arm rigidly connected to the first part, and extending at essentially right angles from the first part, and an additional part engaging a stationary part of a tightening tool so that undesirable rotation movements are prevented during tightening of the screw connection. The additional part which engages the stationary part of the tightening tool during tightening of a screw connection is mounted pivotably on arm and additional part is pivoted relative to arm to allow release of the tightening tool from the holding device after tightening the screw connection.

5 Claims, 1 Drawing Sheet

RELEASABLE HOLDING DEVICE PREVENTING UNDESIRABLE ROTATION DURING TIGHTENING OF A SCREW CONNECTION IN A BONE ANCHORED IMPLANT

FIELD OF THE INVENTION

The present invention relates to a device for use with a tool for mechanical tightening of a screw connection in a bone-anchored dental implant without the tissue which surrounds the implant being stressed. The arrangement will hereinafter be called a counter-holder.

The counter-holder comprises a first part, which is to be rotationally locked to the implant, and a second part forming an arm which is rigidly connected to the first part and which extends out essentially at right angles from the first part and is provided with a part which interacts with the stationary part of the tightening tool so that undesirable rotation movements are prevented during the tightening of the screw connection.

BACKGROUND OF THE INVENTION

A counter-holder of this type is already known from SE 8903797-2 and is used together with drilling equipment during the dental operation for tightening the screw connection which secures the so-called spacer against an anchoring element, preferably a titanium screw, a so-called fixture, implanted in the bone. With this known counter-holder, controlled, mechanical tightening of a screw connection of a dental implant is possible without any torque being taken up by the bone, that is the screw (the fixture) remains unstressed during mounting itself.

As can be seen from FIG. 2 in SE 8903797-2, the counter-holder has a first, tubular part, the base portion of which is provided with an internal space adapted to the spacer so that the spacer is locked and cannot be rotated in relation to the tubular part after the tubular part has been slipped over the spacer. Accordingly, the internal space is in the form of a hexagonal recess in order to fit the cylindrical, hexagonal upper portion of the existing spacers. The internal hole through the tubular part has a diameter such that the screwdriver tool of the drill can rotate freely in this space.

The tubular part is rigidly connected to a fork, the base of which extends essentially at right angles to the center line of the tubular part and the shanks of which are essentially parallel to said center line. The fork is U-shaped and is positioned with one shank on each side of the handpiece of the drill. The shanks have such a length that they extend beyond the diameter of the handpiece. As a result of this, the tightening torque will be taken up by the shanks of the fork instead of stressing the spacer and thus the fixture.

When a predetermined screw tightening torque has been achieved, the handpiece of the tool offers resistance to one shank of the fork. The tightening torque gives rise to a reaction torque which is the same as the tightening torque but in the opposite direction, which means that the tissue which surrounds the implant remains unstressed.

When the predetermined screw tightening torque has been achieved, the tightening tool and the counter-holder are to be removed, which can sometimes be difficult since the handpiece of the tool bears against one shank of the fork with the force which has been built up in the system. When the tool and the counter-holder are to be removed, this force must be released and there is then a risk that the tool or the implant are still stressed inadmissibly.

Instead of the metal spacers which have mainly been used until now, and which are also described in the abovementioned Swedish patent, it is also previously known to use ceramic distance pieces which, like the earlier metal spacers, are secured against the fixture with the aid of a distance screw which is screwed down into a drilled hole in the fixture with the aid of the tightening tool. There are advantages in using ceramic distance pieces instead of the metal distance pieces which were mostly found on the market until now, mainly for aesthetic reasons because the ceramic material is more similar to the surrounding teeth than metal material, but also because the ceramic material can be prepared and more easily individually shaped so that the outer shape of the distance piece is adapted to the anatomical situation in each individual case.

But there are also disadvantages with the ceramic material, mainly in terms of its strength. The material is more brittle and can fracture, especially if too great stresses occur in the material during tightening against the fixture. There is therefore also a risk of fractures in the material when the tool and the counter-holder are to be removed after tightening as a result of the abovementioned "locking" of the tool against one shank of the fork.

SUMMARY OF THE INVENTION

One purpose of this invention is to produce a counter-holder which allows the removal of the tool and the counter-holder after tightening, that is allows the release of the "locking force" which has been built up in the system during tightening.

In one type of ceramic spacer which has now been proposed, the external "counter-holding surfaces" in the form of a hexagonal portion which is present on the metal spacers is also dispensed with instead the ceramic distance piece has an internal channel with counter-holding surfaces, for example a channel with a hexagonal cross-section. This shape means that the counter-holder which is described in the abovementioned Swedish patent cannot be used for tightening the screw connection with a ceramic distance piece as the tubular part in this case has an internal hexagonal recess intended to be slipped over and to interact with the external hexagon of the metal spacers.

A further purpose of this invention is therefore to produce a counter-holder of the abovementioned type which can also be used in tightening screw connections with distance pieces, mainly ceramic, of the type which lacks external counter-holding surfaces in the form of a hexagon or the like.

According to the invention, the counter-holder is characterized in that that part of the arm which is rigidly connected to the first, tubular part, and which interacts with the stationary part of the tightening tool, is movably arranged on the arm in order to allow folding down/stress-relief and release of the tightening tool after tightening has been completed.

This part preferably consists of a U-shaped fork, the fork arranged pivotably on the arm of the counter-holder so that it can be pivoted forwards or backwards and in this manner release the stationary part of the tightening tool.

The invention will be described in greater detail below with reference to the attached drawing which shows a few examples of how the counter-holder can be designed.

DETAILED DESCRIPTION OF THE PREFERRED EMBODIMENTS

Figure 1:
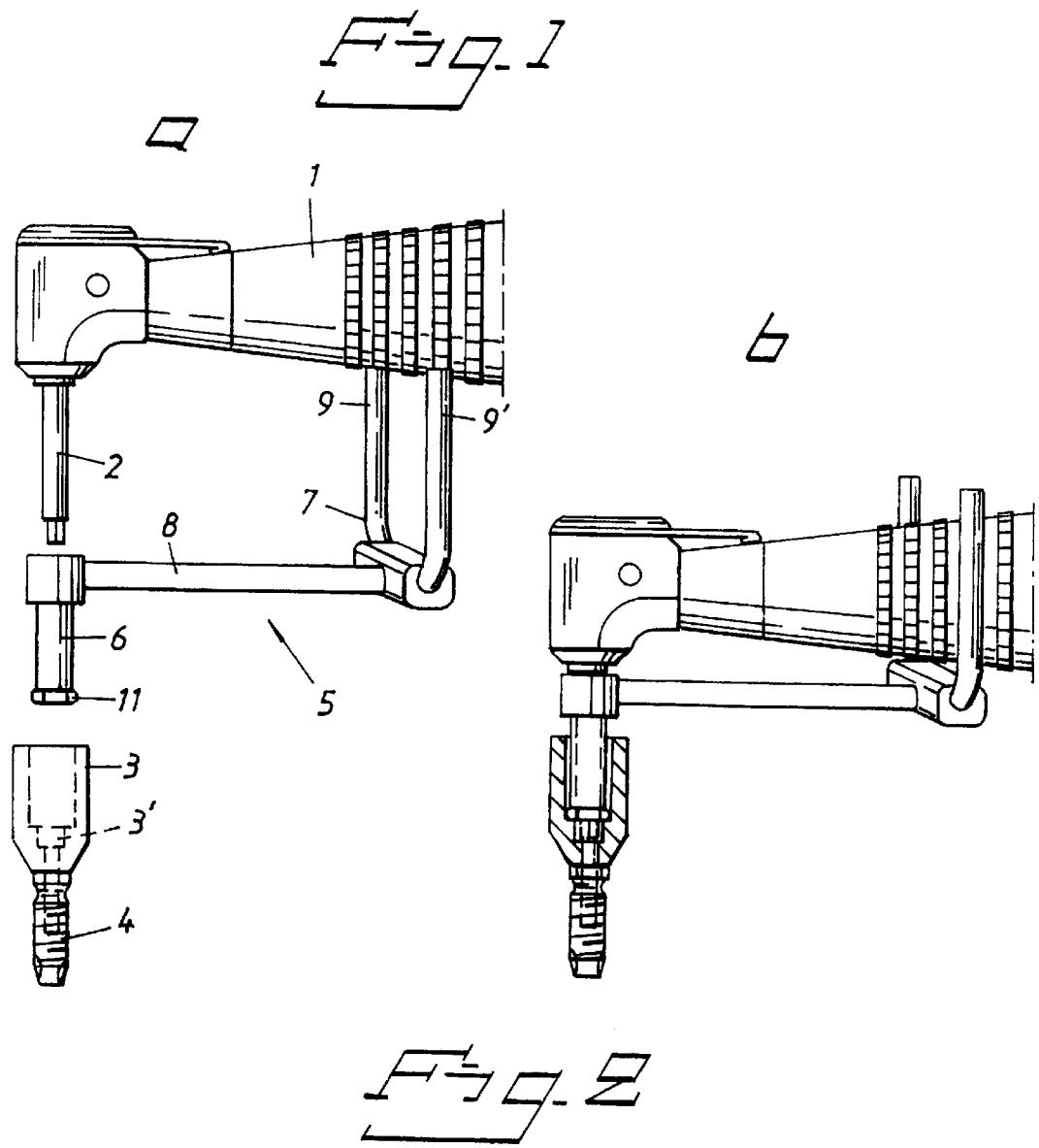
FIG. 1 shows the counter-holder together with a machine for tightening a distance screw in a dental implant.

FIG. 1 shows the handpiece 1 of a drill of a known type which is used in association with dental implant operations. The drill is used for both drilling holes in the jawbone and tightening screw connections in the implant system. In this case, the drill is provided with a screwdriver 2 intended to interact with the screwdriver groove in the distance screw 3' which secures the spacer 3 against the upper portion of the fixture 4. The threaded portion of the distance screw is intended to engage with an internally threaded recess in the upper portion of the fixture for securing the distance piece 3 against the fixture 4.

When the spacer is secured against the fixture, it is important that the screw connection is not tightened so that the bone is stressed via the fixture, which could jeopardize the anchoring of the fixture in the long run. In order to counteract such inadmissible stress, use is made of a so-called counter-holder 5 which consists of a first, tubular part 6, the base of which in use adjoins the distance member and is rotationally locked in relation thereto, and through which the movable part of the drill, the screwdriver 2, can run and rotate freely during tightening, and a second, fork-shaped part 7 which interacts with the stationary part of the drill, the handpiece 1.

As described in greater detail in the abovementioned Swedish patent 8903797-2, the tightening torque does not stress the bone via the fixture as the fork-shaped part 7 interacts with the handpiece 1 and prevents undesirable rotation of the spacer and the fixture.

The fork-shaped part 7 is arranged on an arm 8 which is rigidly connected to the first, tubular part 6 and extends essentially at right angles out from the first part. The fork is U-shaped with a base 7' which extends in the transverse direction in relation to the arm 8 and two shanks 9, 9' of such a length that they extend beyond the diameter of the handpiece 1 of the drill.

The tubular part 6 has a through-channel 10 for the screwdriver tool in which it can run and rotate freely during tightening and a lower portion with an external hexagon 11 intended to engage with a corresponding hexagonal recess in the spacer 3 for rotational locking of the counter-holder in relation to the spacer. In the event that a ceramic spacer is being used, the whole channel as far as the shoulder for the screw head of the distance screw is preferably designed with a hexagonal cross-section, the lower portion 11 of the tubular part 6 engaging with this cross-section while an upper, elongate portion 12, of smaller diameter and without counter-holding surfaces, can run freely in the channel of the spacer. The fact that only the lowest portion 11 of the tubular part 6 of the counter-holder is provided with counter-holding surfaces for rotational locking reduces the risk of fractures in the ceramic material. The lower portion 11 can if appropriate be slotted, that is the six individual counter-holding surfaces are separated by means of slots which makes them somewhat resilient.

FIG. 1 shows the tool, the counter-holder and the implant on the one hand separated (a) and on the other hand while subjected to tightening torque (b) when the screwdriver of the tool is inserted into the tubular part of the counter-holder and the shanks surround the handpiece of the tool.

Figure 2:
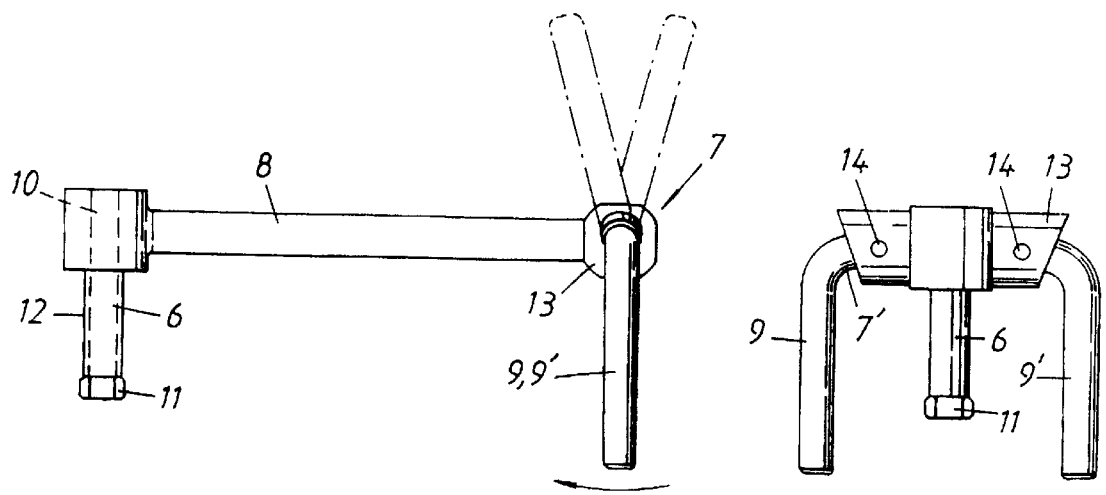
FIG. 2 shows in greater detail how the counter-holder itself can be designed.

As can be seen from FIG. 2, the fork 7 is pivotably mounted on the arm 8 in a bearing 13 in order to allow adjustment (folding up or folding down) of the fork so that both the shanks 9, 9' surround the handpiece 1 while subjected to tightening torque, but are folded away after tightening of the distance screw has been completed in order to allow release of the handpiece 1 of the tightening tool. The fork can be freely pivotable forwards/backwards/round. It can however be spring-loaded so that it assumes a distinct position, for example an upright position, when it is not acted upon and does not fall down by itself. Alternatively, it can assume a folded-down position, as is shown in FIG. 2, the operator folding up the shanks before tightening the distance screw so that they surround the handpiece with one leg on each side and supports them easily with the hand while subjected to tightening torque so that they do not fall down. The bearing 13 itself can consist of a rectangular or cylindrical block which extends in a direction transverse to the arm 8, with a through-channel for the base 7' of the fork, which forms a bearing surface.

In order to allow access for autoclaving steam to the bearing surfaces during the cleaning/sterilizing process, the bearing 11 is provided with one or more through-holes 14 to the through-channel.

The drill is preferably designed in such a manner that when a preset tightening torque has been achieved, the machine stops. In this position, the handpiece of the machine offers resistance to one of the shanks 9, 9' with the force which has been built up in the system. According to the invention, the operator then pivots the fork 7 out of the way so that the handpiece is released and can carefully be lifted away from the distance piece together with the counter-holder. No undesirable bending moment or forces affect the ceramic spacer.

The invention is not limited to the embodiment shown as an example but can be varied within the scope of the patent claims below. For example, to facilitate cleaning, the bearing 13 can be demountable, in which case the base 7' of the fork can be mounted in a recess in the side of the bearing instead of in a channel through it. The fork can then be retained in the recess with the aid of resilient tongues which have been screwed firmly in the bearing piece. In this manner, the abovementioned distinct position can in this case also be obtained for the pivotable fork.

It is also clear that shapes other than hexagons can be used in order to provide the desired locking between the spacer and the counter-holder part.

I claim:

1. Holding device for use with a tool for mechanical tightening of a screw connection in a bone-anchored dental implant without the tissue which surrounds the implant being stressed, said holding device comprising;

a first part having means for rotationally locking to the implant, an arm rigidly connected to the first part, said arm extending at essentially right angles from said first part, and an additional part having means for engaging a stationary part of a tightening tool so that undesirable rotation movements are prevented during tightening of the screw connection, and wherein said additional part having means for engaging the stationary part of the tightening tool is mounted pivotably on said arm and said additional part is pivoted relative to said arm to allow release of the tightening tool from the holding device after tightening the screw connection.

2. Holding device according to claim 1, wherein said additional part has means for engaging the stationary part of the tightening tool comprises a U-shaped fork, said U-shaped fork having a base pivotably mounted in a bearing, said bearing extending at right angles to both said arm and said first part, said U-shaped fork further comprising shanks extending from the base, wherein said U-shaped fork is positioned during tightening of a screw connection so that said shanks are essentially parallel to a longitudinal center line of said first part and engage said stationary part of the tightening tool, thereby holding the stationary part of the tightening tool and preventing undesirable rotation movements, and said U-shaped fork is positioned after tightening of a screw connection so as to disengage shanks from said stationary part of the tightening tool.

3. Holding device according to claim 2, wherein said first part has means for rotationally locking to the implant is tubular, and further comprises a through channel for receiving a screwdriver tool therein, a lower external portion having external counter-holding surfaces corresponding in shape to an internal recess in the screw connection, and an upper elongate portion of smaller diameter than said external portion, wherein only the external portion contacts the internal recess of the screw connection thereby avoiding bearing between the internal recess of the screw connection and said first part.

4. Holding device according to claim 3, wherein said bearing is provided with one or more holes extending into a bearing through channel, thereby allowing access of autoclaving steam or cleaning fluid into the bearing through channel.

5. Holding device according to claim 3, wherein said pivotable fork has biasing means, wherein said biasing means bias said pivotable fork to one or more distinct positions.

\* \* \* \* \*